(12) United States Patent
Harding et al.

(10) Patent No.: US 7,736,340 B2
(45) Date of Patent: Jun. 15, 2010

(54) CATHETER INSERTION DEVICE WITH AUTOMATIC SAFETY BARRIER

(75) Inventors: Weston F. Harding, Lehi, UT (US); Austin Jason McKinnon, Herriman, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 163 days.

(21) Appl. No.: 11/863,847

(22) Filed: Sep. 28, 2007

(65) Prior Publication Data

US 2009/0088696 A1    Apr. 2, 2009

(51) Int. Cl.
*A61M 5/178* (2006.01)
(52) U.S. Cl. .................... 604/164.08; 604/198
(58) Field of Classification Search ............ 604/164.08, 604/198, 110, 192–197
See application file for complete search history.

(56) References Cited

U.S. PATENT DOCUMENTS

| | | | | |
|---|---|---|---|---|
| 4,664,259 A | * | 5/1987 | Landis | ........................ 206/365 |
| 5,051,109 A | | 9/1991 | Simon | |
| 5,139,489 A | * | 8/1992 | Hollister | ..................... 604/192 |
| 5,279,591 A | | 1/1994 | Simon | |
| 5,697,907 A | | 12/1997 | Gaba | |
| 5,718,688 A | | 2/1998 | Wozencroft | |
| 5,853,393 A | * | 12/1998 | Bogert | .................. 604/165.02 |
| 6,254,575 B1 | * | 7/2001 | Thorne et al. | ............... 604/198 |
| 6,298,541 B1 | * | 10/2001 | Newby et al. | .................. 29/458 |
| 6,981,965 B2 | | 1/2006 | Luther et al. | |
| 7,186,239 B2 | | 3/2007 | Woehr | |
| 7,214,211 B2 | | 5/2007 | Woehr et al. | |
| 7,226,434 B2 | | 6/2007 | Carlyon et al. | |
| 7,264,613 B2 | | 9/2007 | Woehr et al. | |
| 7,458,954 B2 | * | 12/2008 | Ferguson et al. | ............ 604/110 |
| 2002/0169418 A1 | | 11/2002 | Menzi et al. | |
| 2003/0144627 A1 | | 7/2003 | Woehr et al. | |
| 2004/0010227 A1 | | 1/2004 | Riesenberger et al. | |
| 2005/0096592 A1 | * | 5/2005 | Carlyon et al. | ............... 604/110 |
| 2006/0270980 A1 | | 11/2006 | Menzi et al. | |
| 2007/0038188 A1 | * | 2/2007 | Bialecki et al. | ......... 604/164.08 |
| 2007/0179447 A1 | | 8/2007 | Carrez et al. | |

* cited by examiner

*Primary Examiner*—Nicholas D Lucchesi
*Assistant Examiner*—Gerald Landry, II
(74) *Attorney, Agent, or Firm*—Mony R. Ghose; Craig Metcalf; Kirton & McConkie (57) ABSTRACT

A catheter insertion device with an automatic safety barrier includes a housing, a barrier member, and a biasing element. The housing includes a central bore configured to receive a needle therethrough, and further includes a channel extending through the housing and intersecting the central bore. The barrier member is hingedly coupled to the housing, and includes a leg to extend through the channel. An opening in the leg substantially aligns with the central bore to accommodate the needle therethrough. The biasing element biases the barrier member relative to the housing such that withdrawing the needle through the opening causes the biasing element to misalign the opening with the central bore, thereby occluding the central bore to shield an end of the needle.

20 Claims, 7 Drawing Sheets

CATHETER INSERTION DEVICE WITH AUTOMATIC SAFETY BARRIER

BACKGROUND

This disclosure relates generally to medical assemblies for the administration of fluids, and more particularly to devices for inserting an intravenous catheter into a patient for fluid administration.

Hypodermic needles are notorious for spreading blood-borne diseases such as Hepatitis B, Hepatitis C, and Human Immunodeficiency Virus ("HIV"), the virus that causes Autoimmune Deficiency Syndrome ("AIDS"). Health care workers are among those most at risk for contracting such diseases, as hypodermic needles are commonly used in medical fields. Needle stick injuries may arise during planned use and exposure, and/or as a result of carelessly or maliciously discarded needles.

The Federal Needle Stick Safety Act was enacted into law on Nov. 6, 2000, and is aimed at reducing the risk to health care workers arising from accidental needle sticks. Among other compliance mandates, the Federal Needle Stick Safety Act requires the use of needles with engineered needle injury protections. Accordingly, many hypodermic needles manufactured today include a needle tip shield or the like to protect against accidental needle sticks.

Of particular concern, however, are injuries from hollow-bore needles, especially those used for blood collection or intravenous ("IV") catheter insertion. These devices are likely to contain residual blood and are associated with an increased risk for HIV transmission. Additionally, devices that require manipulation or disassembly after use, such as hollow-bore needles used for IV catheter insertion, have rates of injury of up to 5.3 times the rate for disposable hypodermic syringes. Such injuries most often occur during or after use and before disposal of the used needle.

IV catheters are traditionally used to infuse fluids, such as saline solution, various medicaments, and/or total parenteral nutrition into a patient. Such catheters may also be used to withdraw blood from a patient, and/or monitor various parameters of the patient's vascular system.

To introduce an IV catheter into a patient, an over-the-needle catheter may be mounted over a hollow-bore introducer needle having a sharp distal tip. The inner surface of the catheter may tightly engage the outer surface of the needle to prevent catheter peelback and facilitate insertion of the catheter into a blood vessel. The tip of the introducer needle may extend beyond the distal tip of the catheter to enable insertion of the catheter at a shallow angle through the patient's skin and into a blood vessel.

To verify proper placement of the needle and catheter in the blood vessel, the clinician may confirm the presence of "flashback" blood in a flashback chamber associated with the catheter and needle assembly. Once proper placement is confirmed, the clinician may then apply pressure to the blood vessel to occlude the vessel, thereby minimizing further blood flow through the introducer needle and catheter. The clinician must then withdraw the needle from the catheter to enable continued access to the blood vessel through the catheter as may be required to infuse fluids or the like. This process of physically manipulating and disassembling the needle and catheter after the needle has been used to position the catheter in a patient's blood vessel creates substantial risks of both accidental needle sticks and exposure to blood and blood contaminants.

From the foregoing discussion, it should be apparent that a need exists for a catheter insertion device with an automatic safety barrier to prevent injury from accidental needle sticks as well as from exposure to biological contaminants. Beneficially, such a device would enable simple and effective operation, minimize an amount of physical manipulation needed to disassemble the needle and catheter after use, and ensure that the end of the needle is properly shielded prior to such disassembly. Such a device is disclosed and claimed herein.

BRIEF SUMMARY

The present invention has been developed in response to the present state of the art, and in particular, in response to the problems and needs in the art that have not yet been met by currently available catheter insertion devices. Accordingly, the present invention has been developed to provide an apparatus, system, and method for shielding an end of a needle that overcomes many or all of the above-discussed shortcomings in the art.

An apparatus to shield an end of a needle in accordance with embodiments of the present invention may include a housing, a barrier member, and a biasing element. The housing may include a central bore configured to receive a needle therethrough. The housing may further include a channel extending through the housing and intersecting the central bore.

The barrier member may be hingedly coupled to the housing, and may include a leg to extend through the channel. An opening in the leg may substantially align with the central bore to accommodate the needle therethrough. In one embodiment, the leg of the barrier member includes a lock feature to prevent withdrawing the leg through the channel upon withdrawing the needle through the opening. In other embodiments, the leg further includes a single-use feature to cooperate with the lock feature to automatically limit movement between the barrier member and the housing upon withdrawing the needle through the opening.

The biasing element may bias the barrier member relative to the housing such that withdrawing the needle through the opening causes the biasing element to misalign the opening with the central bore, thereby occluding the central bore to shield an end of the needle. The needle may include a securing feature to prevent withdrawing the end of the needle through a proximal end of the housing.

In some embodiments, an apparatus in accordance with the present invention may further include a catheter to connect to a distal end of the housing such that the catheter may receive the needle through the central bore. In certain embodiments, the barrier member includes a retention hook that releasably secures the catheter to the housing. The retention hook may automatically release the catheter from the housing upon withdrawing the needle through the opening.

A method to shield an end of a needle in accordance with embodiments of the present invention is also presented. The method may include providing a housing having a central bore configured to receive a needle therethrough. A channel may be integrated into the housing to extend through the housing and intersect the central bore. A barrier member may be hingedly coupled to the housing and may include a leg to extend through the channel. An opening in the leg may substantially align with the central bore to accommodate the needle therethrough. The barrier member may be biased relative to the housing such that withdrawing the needle through the opening causes the opening to misalign with the central bore, thereby occluding the central bore to shield an end of the needle. In one embodiment, a misaligned position of the opening relative to the central bore may be substantially secured upon withdrawing the needle through the opening.

In some embodiments, the method may further include actuating the barrier member such that the leg extends through the channel. The opening in the leg may be substantially aligned with the central bore to accommodate the needle therethrough, and the needle may be inserted through the central bore and the opening.

In one embodiment, the method further includes attaching a catheter to a distal end of the housing such that the catheter communicates with the needle through the central bore. The catheter may be releasably secured to the housing via the barrier member. Specifically, a retention hook coupled to the barrier member may be actuated to secure the catheter to the housing by inserting the needle through the opening. The catheter may be automatically released from the housing upon withdrawing the needle through the opening.

A system to shield an end of a needle in accordance with the present invention may include piercing means for piercing a blood vessel to acquire intravenous access, and housing means for housing the piercing means. Barrier means may selectively occlude a portion of the housing means to shield an end of the piercing means. The barrier means may be hingedly coupled to the housing means, and may include a leg to extend through the housing means. An opening in the leg may substantially align with a bore in the housing means to accommodate the piercing means therethrough.

Biasing means may bias the barrier means relative to the housing means such that withdrawing the piercing means through the opening causes the biasing means to misalign the opening with the bore. In this manner, embodiments of the present invention may occlude a portion of the bore to shield an end of the piercing means. In some embodiments, the piercing means may include a securing feature to prevent withdrawing an end thereof through a proximal end of the housing means.

The system may further include communication means for communicating fluids between the blood vessel and an external source. The communication means may selectively connect to a distal end of the housing means such that the piercing means may communicate with the communication means through the housing means. In one embodiment, the system further includes retention means for releasably retaining the communication means with respect to the housing means in response to insertion of the piercing means through the opening. Certain embodiments of the system may also include locking means for automatically limiting movement between the barrier means and the housing means upon withdrawing the piercing means through the opening.

These and other features and advantages of the present invention may be incorporated into certain embodiments of the invention and will become more fully apparent from the following description and appended claims, or may be learned by the practice of the invention as set forth hereinafter. The present invention does not require that all the advantageous features and all the advantages described herein be incorporated into every embodiment of the invention.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings, in which.

DETAILED DESCRIPTION

The illustrated embodiments of the present invention will be best understood by reference to the drawings, wherein like parts are designated by like numerals throughout. It will be readily understood that the components of the present invention, as generally described and illustrated in the Figures herein, may be arranged and designed in a wide variety of different configurations. Thus, the following more detailed description, as presented in the Figures, is not intended to limit the scope of the invention as claimed, but is merely representative of selected embodiments of the invention. The following description is intended only by way of example, and simply illustrates certain selected embodiments of devices, systems, and processes that are consistent with the invention as claimed herein.

As used in this specification, the term "needle" refers to any of various devices that may be used to pierce the skin to acquire intravenous access, such as a hypodermic needle, a hollow-bore needle, a surgical knife, a cannula, or the like.

Figure 1:
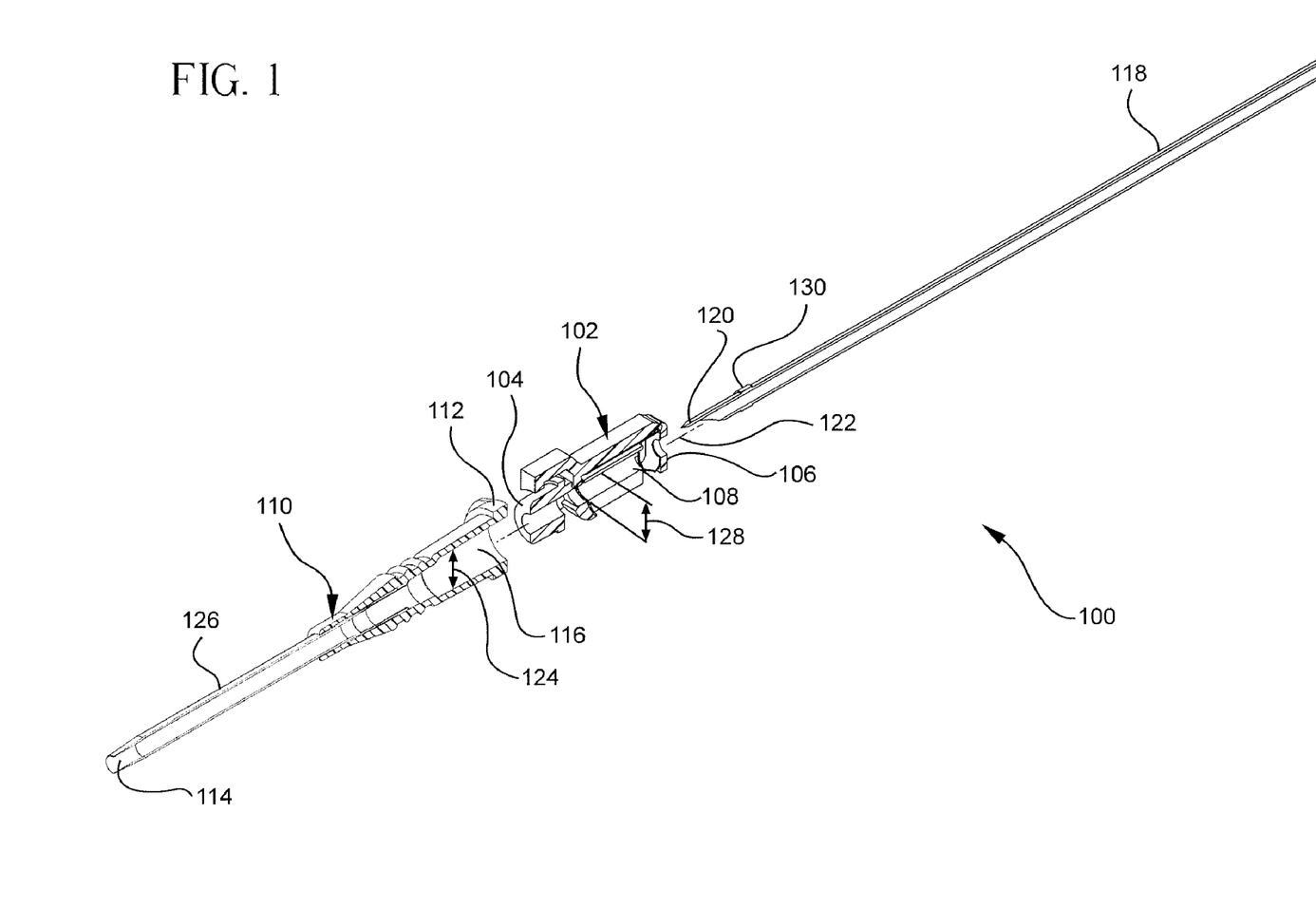
FIG. 1 is an exploded cross-sectional view of a catheter insertion device with an automatic safety barrier in accordance with certain embodiments of the present invention.

Referring now to FIG. 1, a catheter insertion device 100 in accordance with the present invention may include a safety barrier device 102, a catheter 110, and a needle 118. The safety barrier device 102, catheter 110, and needle 118 may align with each other along a longitudinal axis 122. A proximal end 112 of the catheter 110 may attach to a distal end 104 of the safety barrier device 102 by way of, for example, a threaded connection, a press fit, or by any other means known to those in the art. The needle 118 may be directed through the central bores 108, 116 of each of the safety barrier device 102 and the catheter 110, respectively, such that the tip 120 of the needle 118 may protrude through a distal end 114 of the catheter 110 to facilitate an intravenous catheterization process.

The central bore 116 of the catheter 110 may include a diameter 124 slightly larger than an outside diameter 126 of the needle 118. In certain embodiments, a distal portion 126 of the central bore 116 may tightly engage the needle 118 to prevent peelback of the catheter 110 as it is inserted into a blood vessel. In some embodiments, the inside diameter 124 of the catheter 110 may increase between the distal portion 126 and the proximal end 112, such that the diameter 124 substantially matches an inside diameter 128 of the central bore 108 of the safety barrier device 102 at a point of attachment between the two devices 110, 102.

In any case, the inside diameters 124, 128 of the central bores 116, 108 may permit the needle 118 to slide with respect to the catheter 110 and safety barrier device 102. In some embodiments, the central bores 116, 108 may include a substantially smooth inner surface to further facilitate relative movement between the needle 118 and the catheter 110 and safety barrier device 102. In this manner, the needle 118 may be selectively positioned to protrude from the distal end 114 of the catheter 110 as needed to facilitate catheter 110 insertion. Likewise, the needle 118 may be selectively retracted from the proximal end 112 of the catheter 110 after use. In one embodiment, as discussed in more detail below, the needle 118 includes a securing feature 130 to prevent the tip 120 of the needle 118 from being intentionally or inadvertently withdrawn from the safety barrier device 102 after use.

Figures 2, 3:
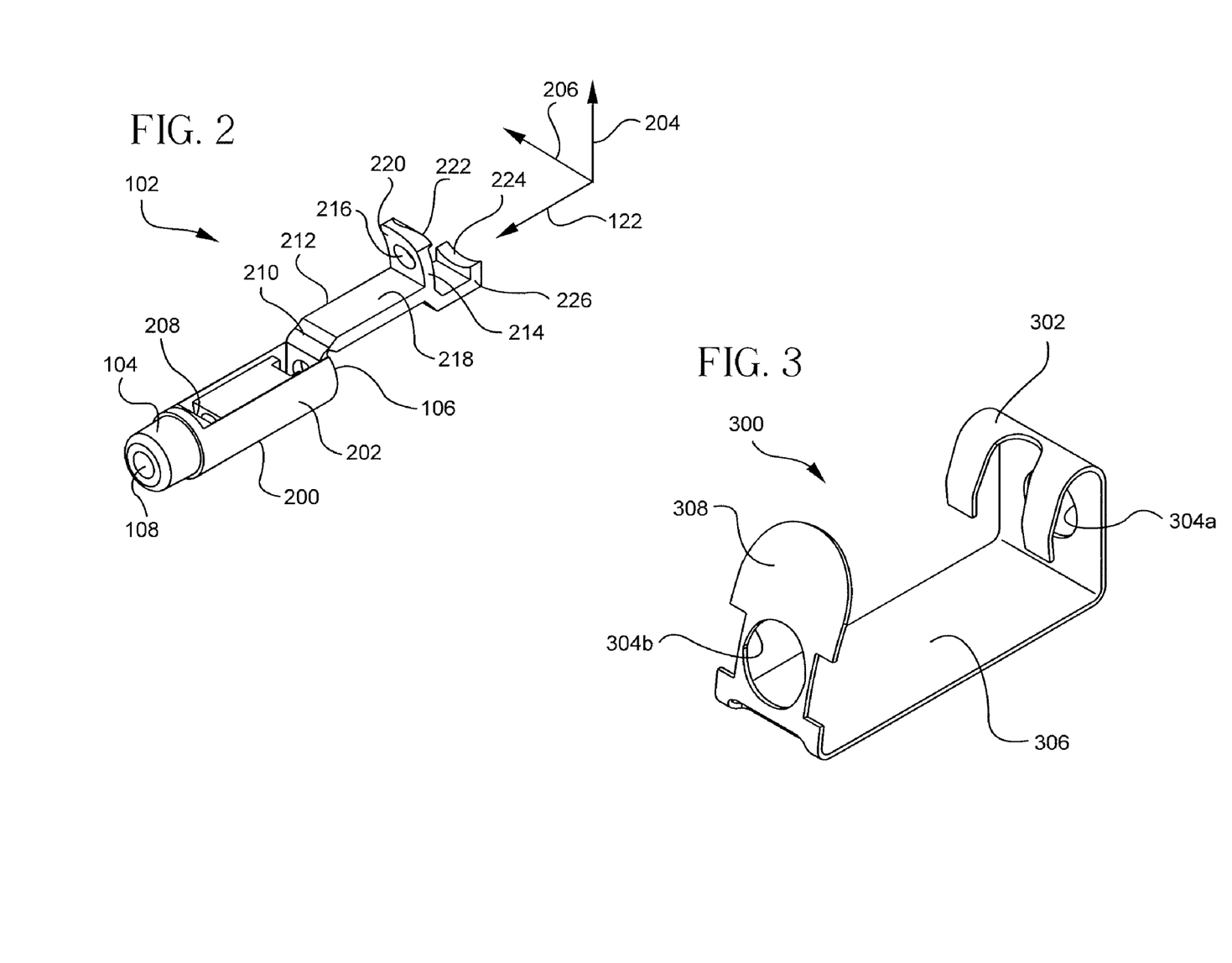
FIG. 2 is a perspective view of one embodiment of a safety barrier device integral to the catheter insertion device of the present invention.
FIG. 3 is a perspective view of one embodiment of a biasing element that may be integrated into a safety barrier device in accordance with the invention.

Referring now to FIG. 2, in discussing the Figures, it may be advantageous to establish a reliable coordinate system to aid in the description of several of the embodiments in accordance with the present invention. In addition to the longitudinal axis 122 discussed above with reference to FIG. 1, coordinate axes may include a transverse axis 204 and a lateral axis 206, where each coordinate axis 122, 204, 206 extends in a direction substantially orthogonal to the other.

A safety barrier device 102 in accordance with the present invention may include a housing 200, a barrier member 212, and a biasing element (not shown). In one embodiment, an outer surface 202 of the housing 200 may be substantially cylindrical and molded along the longitudinal axis 122 to provide a secure, comfortable grip. In some embodiments, for example, the housing 200 may include grooves, ridges or an otherwise textured outer surface 202 to facilitate a secure grip.

The central bore 108 may extend in a substantially longitudinal direction 122 from a distal end 104 to a proximal end 106 of the housing 200. The proximal end 106 of the housing 200 may be configured to direct the needle 118 into the central bore 108. In some embodiments, the needle 118 may extend through the central bore 108 and exit the housing 200 at its distal end 104 to communicate with a catheter 110 or other device attached thereto.

In one embodiment, a diameter 128 of the central bore 108 may taper from the distal end 104 to the proximal end 106 of the housing 200. In other embodiments, a diameter 128 of the central bore 108 at the proximal end 106 of the housing 200 may be substantially less than its diameter 128 at the distal end 104 of the housing 200, or at an intermediate point along its longitudinal axis 204*a*. In still other embodiments, a diameter 128 of the central bore 108 may be substantially consistent along a length of the housing 200.

The barrier member 212 may attach to a proximal end 106 of the housing 200 by way of a hinge 210 or other such device known to those in the art. In one embodiment, the barrier member 212 and housing 200 are substantially monolithic, having a living hinge 210 or flexure bearing therebetween. Alternatively, the housing 200 and barrier member 212 may constitute separate components attached by a standard hinge 210 or other suitable device known to those in the art. In any case, the hinge 210 may permit the barrier member 212 to pivot with respect to the housing 200, such that a leg 214 of the barrier member 208 may selectively extend into a channel 208 formed within the housing 200.

The channel 208 may extend in a substantially transverse direction 204 through the housing 200 and intersect the central bore 108. In one embodiment, the channel 208 opens onto substantially opposite sides of the housing 200. In other embodiments, the channel 208 extends only partially through the housing 200 such that a single point of entry on the outer surface 202 of the housing 200 provides access to the channel 208. In any case, the channel 208 may include a length sufficient to accommodate the leg 214 of the barrier member 212.

The leg 214 of the barrier member 212 may extend from the body 218 of the barrier member 212 such that pivoting the barrier member 212 with respect to the housing 200 may cause the leg 214 to extend into the channel 208. The leg 214 of the barrier member 212 may include an opening 216 that may align with the central bore 108. Further, the opening 216 may include a diameter substantially corresponding to a diameter 128 of the central bore 108. In this manner, the needle 118 may be advanced through the opening 216 to secure the leg 214 with respect to the channel 208, as discussed in more detail with reference to FIGS. 4 and 5 below.

The leg 214 of the barrier member 212 may include a safety barrier portion 220 to selectively block the central bore 108, or portion thereof. In certain embodiments, as discussed in more detail below, the biasing element (not shown) may cooperate with the barrier member 212 to automatically misalign the opening 216 with the central bore 108 upon withdrawing the tip 120 of the needle 118 from the opening 216. The safety barrier portion 220 of the leg 214 may then occlude the central bore 108 at the channel 208 to prevent access to the needle 118 through the distal end 104 of the housing 200. In some embodiments, as discussed in more detail below, the leg 214 of the barrier member 212 may include a lock feature 222 to maintain the leg 214 within the channel 208 upon withdrawing the needle 118 from the opening 216.

The barrier member 212 may further include a retention hook 224 extending from a distal end 226 thereof. As discussed in more detail below, the retention hook 224 may secure the catheter 110 or other device to the safety barrier device 102 by creating mechanical interference between the barrier member 212 and the proximal end 112 of the catheter 110 or other attached device.

Referring now to FIG. 3, a biasing element 300 in accordance with the present invention may include a spring, an elastomeric material, a resilient material, or any other suitable material or device known to those in the art. The biasing element 300 may include an attachment feature 302 to attach the biasing element 300 to the safety barrier device 102. The biasing element 300 may cooperate with the barrier member 112 to urge the barrier member 112 away from the housing 200 absent application of an opposite force. The barrier member 112 may be secured in a biased position relative to the housing 102 by extending the needle 118 through the central bore 108 and opening 216 to apply an opposite force.

Specifically, in one embodiment, the biasing element 300 includes a leaf-spring portion 306 residing substantially adjacent to the body 218 of the barrier member 212 to urge the barrier member 212 away from the housing 200. The biasing element 300 may be attached to the housing 200 by way of an attachment feature 302 such as a retention hook or other suitable device known to those in the art. The needle 118 may extend through the central bore 108 and the opening 216 in the leg 214 of the barrier member 212 to maintain the central bore 108 and opening 216 in alignment, thereby securing the barrier member 212 in a biased position relative to the housing 200. In certain embodiments, such as where the biasing element 300 or attachment feature 302 would otherwise obstruct the central bore 108, the biasing element 300 may include an opening 304 to accommodate the needle 118 therethrough.

Figure 4:
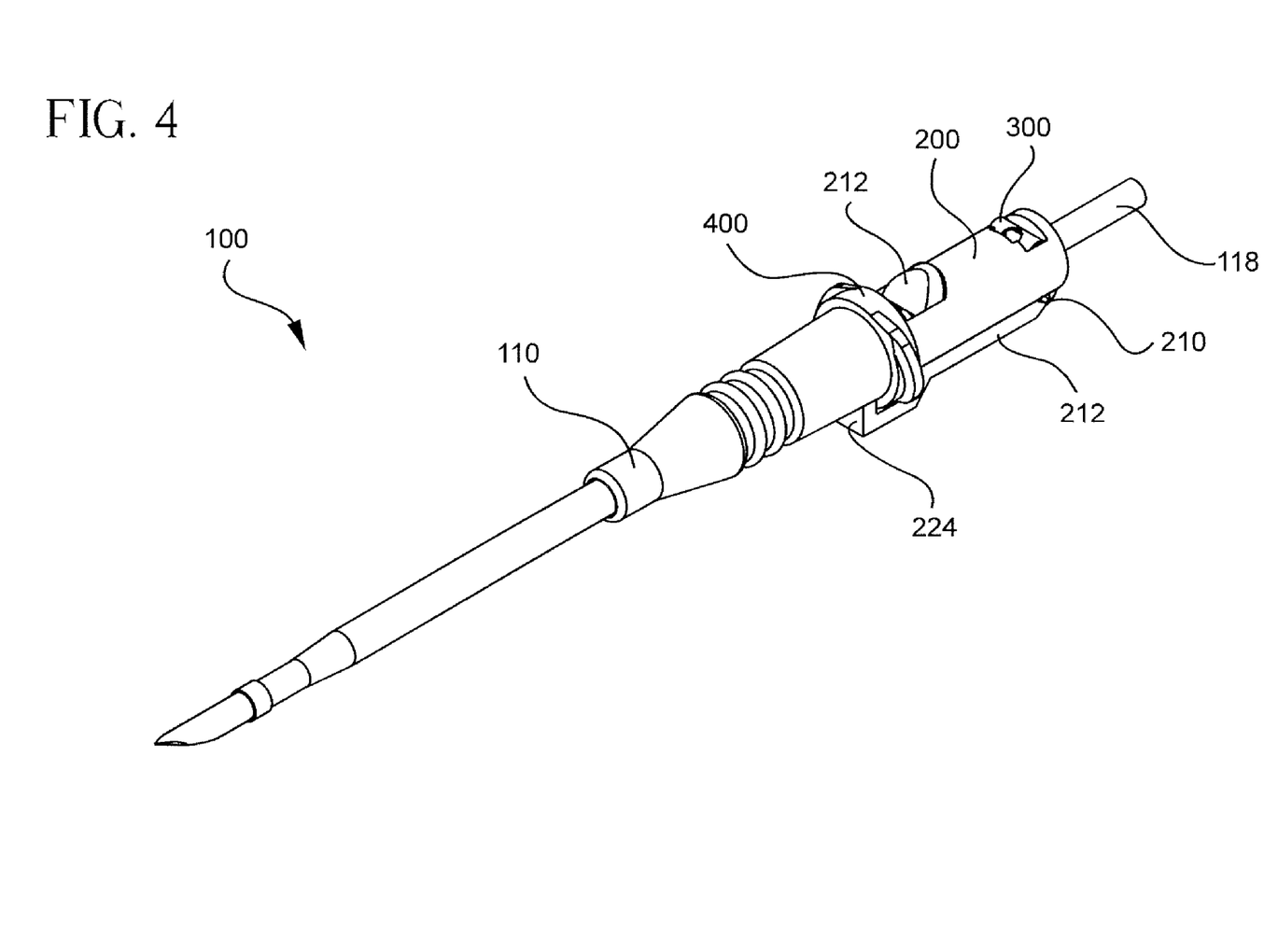
FIG. 4 is a perspective view of a catheter insertion device armed for use in accordance with certain embodiments of the present invention.
Figure 5:
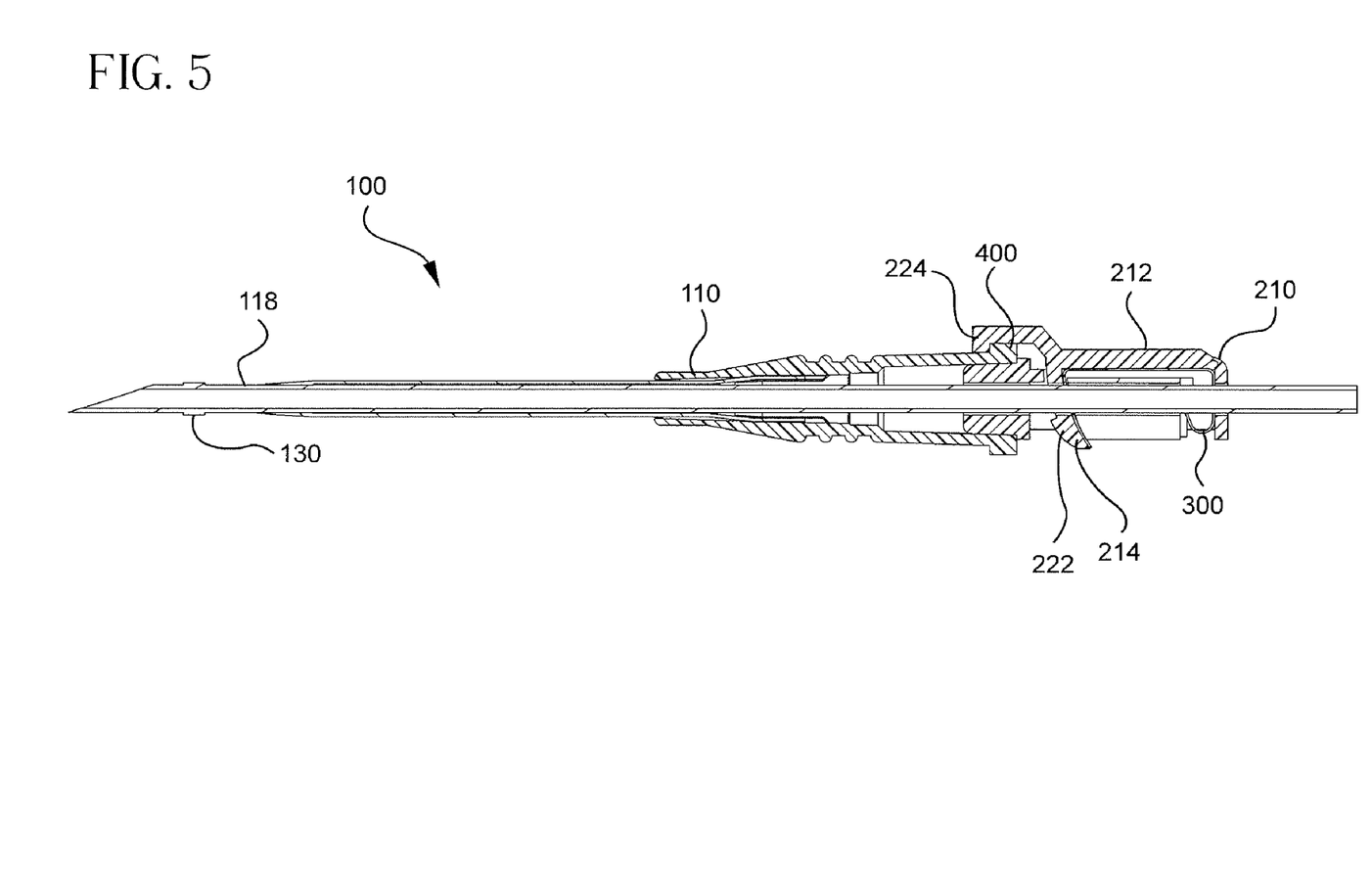
FIG. 5 is a cross-sectional view of the catheter insertion device of FIG. 4.

Referring now to FIGS. 4 and 5, the catheter insertion device 100 of the present invention may be armed to effectively shield a tip 120 of a needle 118 by attaching a catheter 110 or other adapter device to a distal end 104 of the housing 200 and pivoting the barrier member 212 with respect to the housing 200 such that a leg 214 thereof may be received into the channel 208. As previously discussed with reference to FIG. 3 above, a biasing element 300 may be integrated with the housing 200 to urge the barrier member 212 away from the housing 200. Accordingly, pivoting the barrier member 212 towards the housing 200 to enable the leg 214 to be received into the channel 208 may require application of an opposing force. The force applied may be adjusted as needed to position the leg 214 such that an opening 216 in the leg 214 may substantially align with the central bore 108. The needle 118 may then be inserted into the central bore 108 through a proximal end 106 of the housing 200 and advanced through the central bore 108 and opening 216 in the leg 214.

In some embodiments, the needle 118 may be further guided through the distal end 104 of the housing and into the attached catheter 110 or other device. In one embodiment, the needle 118 protrudes through the distal end 114 of the catheter 110 to facilitate an intravenous catheterization process. In this manner, the needle 118 may maintain alignment between the central bore 108 and the opening 216, thereby securing a position of the leg 214 with respect to the channel 208.

Moreover, in some embodiments, the needle 118 may maintain a substantially fixed relationship between a retention hook 224 extending from a distal end 226 of the barrier member 212 and the catheter 110 or other adapter device attached to the housing 200. Specifically, in some embodiments, the catheter 110 or other adapter device may include a lip 400 extending substantially radially from its proximal end 112. The retention hook 224 may be molded to interlock with the lip 400 where the catheter 110 attaches to the distal end 104 of the housing 200. As the retention hook 224 is integral to the barrier member 212, the needle 118 may extend through the opening 216 in the leg 214 of the barrier member 212 to both maintain alignment between the central bore 108 and the opening 216, as well as to secure an interlocked relationship between the retention hook 224 and the lip 400 of the catheter 110. Accordingly, attachment of the catheter 110 to the housing 200 may also be reliably secured.

Figure 6:
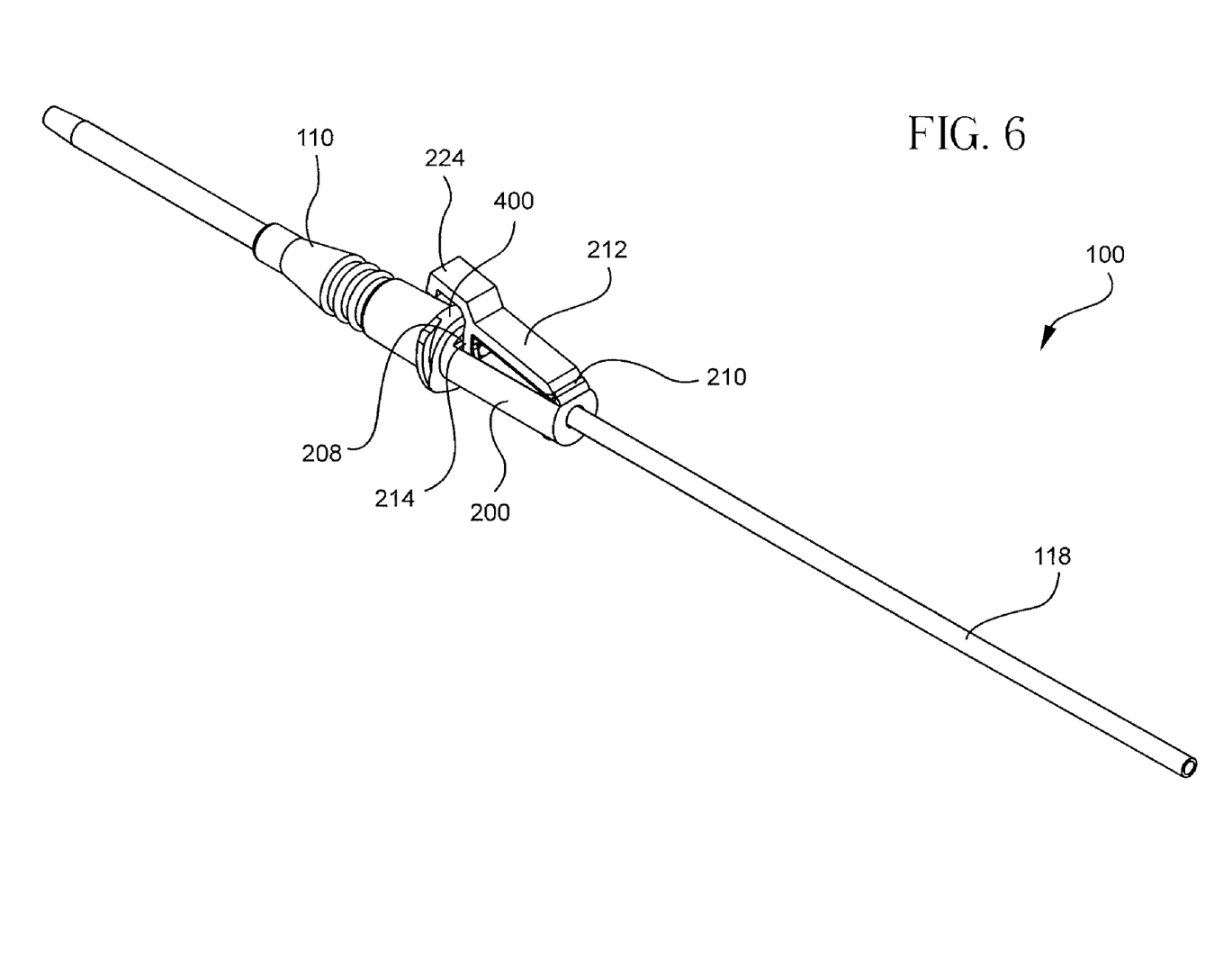
FIG. 6 is a perspective view of one embodiment of a catheter insertion device after use in accordance with the present invention.
Figure 7:
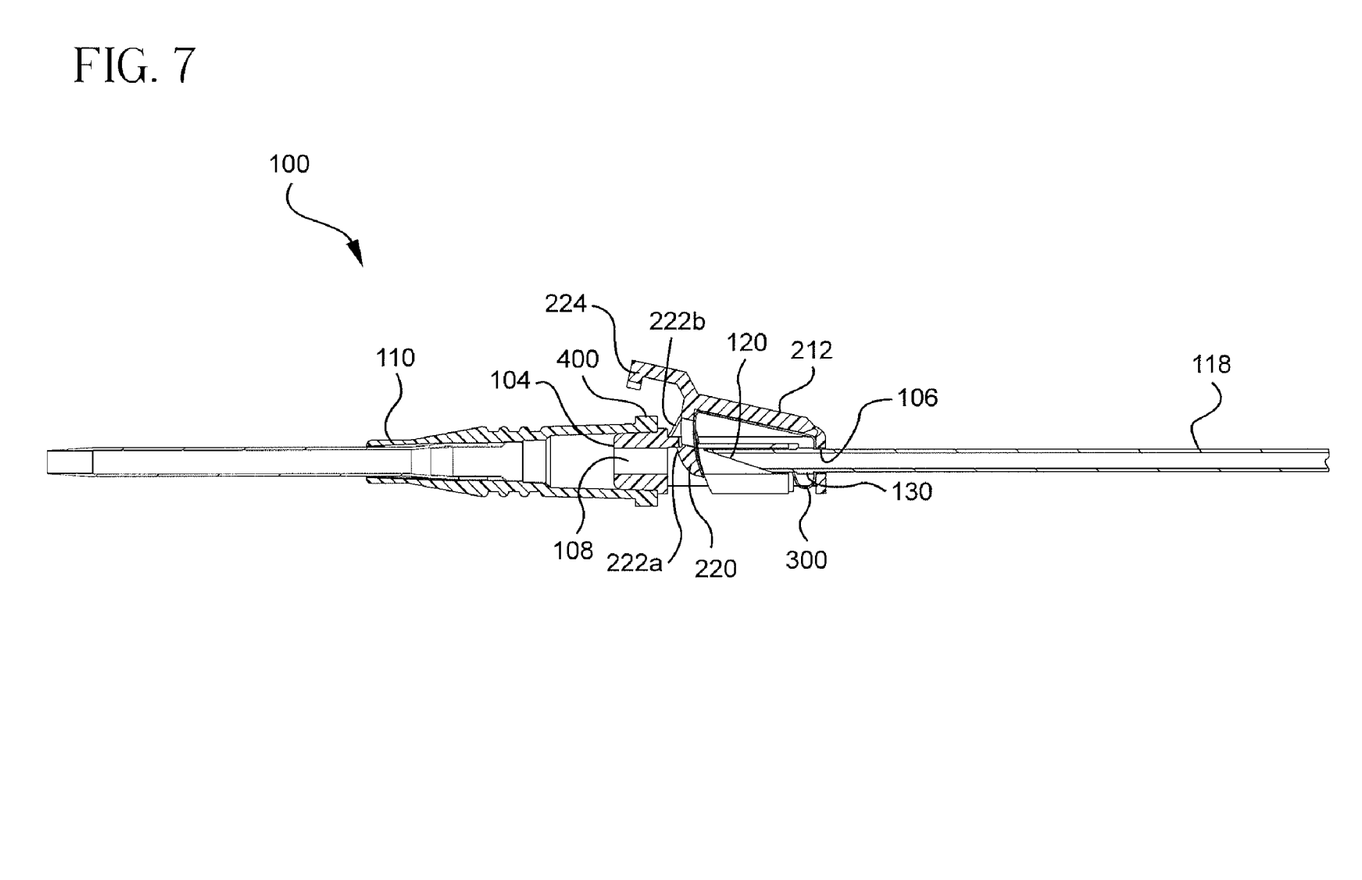
FIG. 7 is a cross-sectional view of the catheter insertion device of FIG. 6.

Referring now to FIGS. 6 and 7, retracting the needle 118 through the opening 216 in a longitudinal direction 122 towards the proximal end 106 of the housing 200 may actuate the biasing element 300 to urge the barrier member 212 away from the housing 200, thereby misaligning the opening 216 with the central bore 116. As a result, a safety barrier portion 220 of the leg 214 positioned adjacent to the opening 216 may be forced to fully or partially occlude the central bore 108. As previously mentioned, a lock feature 222 coupled to the leg 214 may abut or otherwise mechanically interfere with a portion of the housing 200 to prevent withdrawal of the safety barrier portion 220 of the leg 214 from the channel 208. In certain embodiments, the lock feature 222 may include cooperating features 222a, 222b substantially adjacent either side of the opening 216, such that withdrawing the needle 118 through the opening 216 may actuate the cooperating lock features 222a, 222b to limit movement of the leg 214 with respect to the channel 208 in either transverse direction 204. In this manner, the lock feature 222 may reliably secure the safety barrier portion 220 to at least partially occlude the central bore 108 and thus prevent the retracted needle tip 120 from re-entering the central bore 108 at a position longitudinally distal from the channel 208.

In certain embodiments, retracting the needle 118 through the opening 216 may further disengage the interlocked relationship between the retention hook 224 and the proximal end 112 of the catheter 110. Specifically, the biasing element 300 may urge the barrier member 212 and retention hook 224 away from the housing 200 and attached catheter 110. The retention hook 224 may thus release the proximal end 112 of the catheter 110 to enable the catheter 110 and safety barrier device 102 to be disassembled after use.

As discussed above, retracting the needle 118 through the opening 216 towards the proximal end 106 of the housing 200 effectively occludes the central bore 108 while releasing the catheter 110 from the distal end 104 of the housing 200. As a result, embodiments of the present invention provide increased protection against accidental needle sticks and blood exposure by ensuring both proper shielding of the needle tip 120 after use, as well as by preventing disassembly of the catheter insertion device 100 prior to the needle tip 120 being properly shielded.

In certain embodiments of the present invention, the needle 118 may include a securing feature 130 to prevent complete withdrawal of the needle 118 through the proximal end 106 of the housing 200. The securing feature 130 may include, for example, one or more protrusions from the needle 118 surface, an increased diameter of the needle 118 at a particular point along its longitudinal axis 122, or any other suitable securing feature known to those in the art. The securing feature 130 may interfere with the central bore 108 at a proximal end 106 of the housing 200 such that the needle tip 120 may not be withdrawn from the central bore 108 at the proximal end 106.

Figure 8:
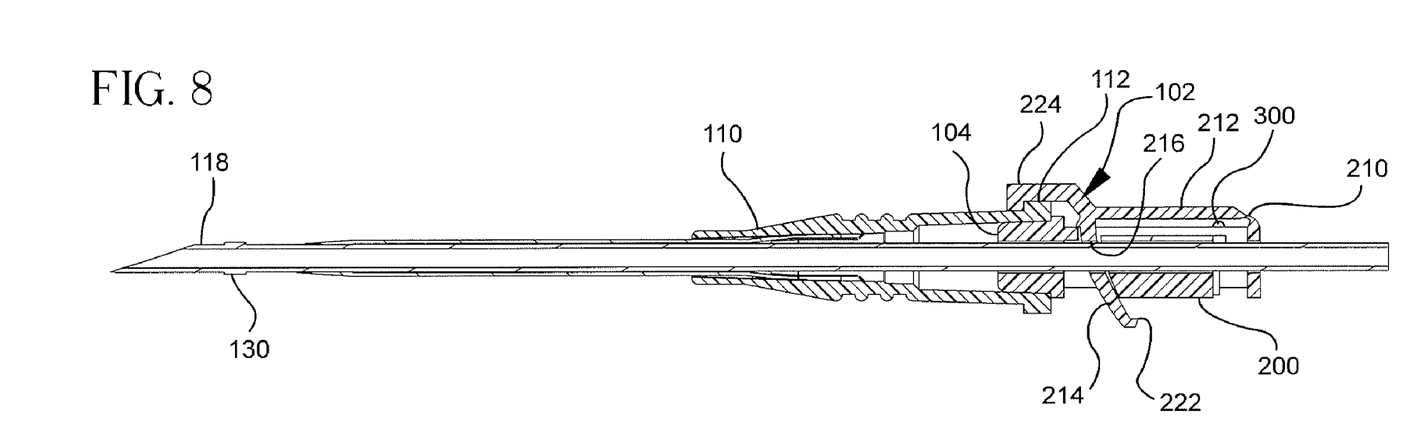
FIG. 8 is a cross-sectional view of an alternative embodiment of a catheter insertion device with an automatic safety barrier armed in accordance with the present invention.
Figure 9:
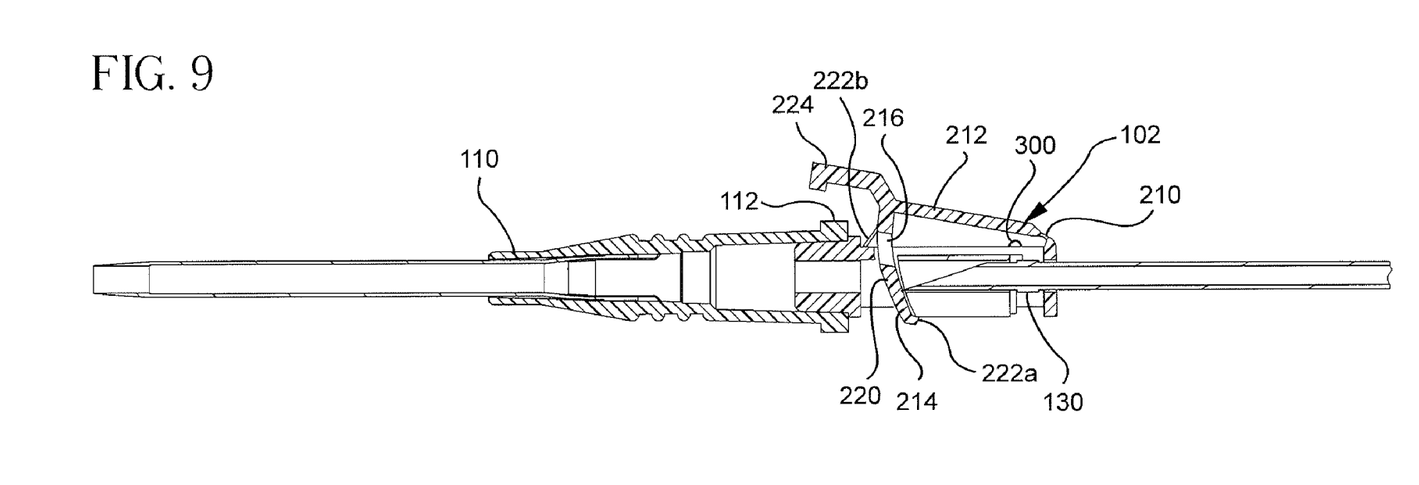
FIG. 9 is a cross-sectional view of the catheter insertion device of FIG. 7 after use.

Referring now to FIGS. 8 and 9, an alternative embodiment of a safety barrier device 102 in accordance with the present invention may include a housing 200, a barrier member 212, and a biasing element 300, where the biasing element 300 includes a protrusion or other feature on the outer surface 202 of the housing located proximate to a hinge 210 connecting the housing 200 and barrier member 212. The barrier member 212 may include a resilient material to enable the barrier member 212 to flex outwardly against the biasing element 300, thereby generating spring energy. This may occur, for example, where the barrier member 212 pivots with respect to the housing 200 to enable a leg 214 thereof to extend through a channel 208 extending in a substantially transverse direction 204 through the housing 200.

Such spring energy may be stored by the barrier member 212 as a result of the needle 118 extending through the central bore 108 of the housing, and further through the opening 216 in the leg 214 of the barrier member 212 to maintain alignment between the central bore 108 and the opening 216. In this position, the needle 118 may further secure a proximal end 112 of the catheter 110 to a distal end 104 of the housing 200 by actuating a retention hook 224 integrated with or coupled to a distal end of the barrier member 212. As discussed above, the retention hook 224 may interface with the proximal end 112 of the catheter 110 to secure its position relative to the distal end 104 of the housing 200.

Referring now to FIG. 9, withdrawing the needle 118 from the opening 216 in the leg 214 of the barrier member 212 may actuate a lock feature 222 integrated with or coupled to the leg 214. The lock feature 222 may secure misalignment of the opening 216 and the central bore 108 within the channel 208 such that a safety barrier portion 220 of the leg 214 effectively and reliably obstructs the needle tip 120 relative to a distal end 104 of the central bore 108.

As illustrated, the lock feature 222 may include cooperating lock features 222a, 222b, located substantially adjacent either side of the opening 216. One lock feature 222a may interface with an outer surface 202 of the housing 200, while the other lock feature 222b interfaces with a substantially opposite surface 202 of the housing 200. The lock features 222a, 222b may be actuated in response to misalignment between the central bore 108 and the opening 216. Specifically, the biasing element 300 may urge the barrier member 212 in a substantially transverse direction 204 away from the longitudinal axis 122 of the housing 200, thereby misaligning the central bore 108 and opening 216 to actuate the lock features 222a, 222b.

In one embodiment, one lock feature 222a may be molded to project from a distal end of the leg 214 of the barrier member 212 and abut the outer surface 202 of the housing 200, while a second lock feature 222b may selectively protrude from the leg 214 upon misalignment of the central bore 108 with the opening 216. Specifically, the second lock feature 222b may be biased with respect to the leg 214 such that the lock feature 222b automatically protrudes outwardly from the leg 214 upon its emergence from within the channel 208. The lock features 222a, 222b may thus cooperate to limit movement of the leg 214 in either transverse direction 204 relative to the housing 200. In this manner, embodiments of the present invention may prevent complete withdrawal of the leg 214 from within the channel 208 to reliably shield a tip 120 of the needle 118, as well as discourage re-use of the catheter insertion device 100.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. An apparatus to shield an end of a needle, the apparatus comprising:
   a housing having a central bore configured to receive a needle therethrough, the housing further having a channel extending through the housing and intersecting the central bore;
   a barrier member coupled to the housing by a living hinge and comprising a leg to extend through the channel, wherein an opening in the leg substantially aligns with the central bore to accommodate the needle therethrough; and
   a biasing element to bias the barrier member relative to the housing, wherein withdrawing the needle through the opening causes the biasing element to move the barrier member into a position in which misalign the opening is misaligned with the central bore, thereby occluding the central bore to shield an end of the needle.

2. The apparatus of claim 1, further comprising a catheter to connect to the housing at a distal end thereof, wherein the catheter communicates with the needle through the central bore.

3. The apparatus of claim 2, wherein the barrier member further comprises a retention hook to releasably secure the catheter to the housing.

4. The apparatus of claim 3, wherein the retention hook automatically releases the catheter from the housing upon withdrawing the needle through the opening.

5. The apparatus of claim 1, wherein the leg of the barrier member further comprises a lock feature adapted to prevent withdrawing the leg through the channel upon withdrawing the needle through the opening.

6. The apparatus of claim 5, wherein the leg of the barrier member further comprises a single-use feature to cooperate with the lock feature to automatically limit movement between the barrier member and the housing upon withdrawing the needle through the opening.

7. The apparatus of claim 1, wherein the needle comprises a securing feature to prevent withdrawing the end of the needle through a proximal end of the housing.

8. A method to shield an end of a needle, the method comprising:
   providing a housing having a central bore configured to receive a needle therethrough;
   integrating into the housing a channel to extend through the housing and intersect the central bore;
   coupling to the housing a barrier member by a living hinge, the barrier member having a leg to extend through the channel, wherein an opening in the leg substantially aligns with the central bore to accommodate the needle therethrough; and
   biasing the barrier member relative to the housing, wherein withdrawing the needle through the opening causes the barrier member to move to a position where the opening to is misaligned with the central bore, thereby occluding the central bore to shield an end of the needle.

9. The method of claim 8, further comprising:
   actuating the barrier member such that the leg extends through the channel;
   substantially aligning the opening in the leg with the central bore to accommodate the needle therethrough; and
   inserting the needle through the central bore and the opening.

10. The method of claim 8, further comprising attaching a catheter to a distal end of the housing, wherein the catheter communicates with the needle through the central bore.

11. The method of claim 10, further comprising automatically releasably securing the catheter to the housing via the barrier member.

12. The method of claim 11, wherein automatically releasably securing the catheter to the housing comprises automatically actuating a retention hook coupled to the barrier member by inserting the needle through the opening.

13. The method of claim 11, further comprising automatically releasing the catheter from the housing upon withdrawing the needle through the opening.

14. The method of claim 8, further comprising substantially securing a misaligned position of the opening relative to the central bore upon withdrawing the needle through the opening.

15. A system to shield an end of a needle, the system comprising:
   piercing means for piercing a blood vessel to acquire intravenous access;
   housing means for housing at least a portion of the piercing means;
   barrier means for selectively occluding at least a portion of the housing means to shield an end of the piercing means, wherein the barrier means is coupled to the housing means by a living hinge, the barrier means comprising a leg to extend through the housing means, and further comprising an opening in the leg to substantially align with a bore in the housing means to accommodate the piercing means therethrough; and biasing means for biasing the barrier means relative to the housing means, wherein withdrawing the piercing means through the opening causes the biasing means to move the barrier member into a position in which the opening is misaligned with the bore, thereby occluding at least a portion of the bore to shield an end of the piercing means.

16. The system of claim 15, further comprising communication means for communicating fluids between the blood vessel and an external source, wherein the communication means selectively connects to a distal end of the housing means.

17. The system of claim 16, wherein the piercing means communicates with the communication means through the housing means.

18. The system of claim 15, further comprising retention means for releasably retaining the communication means with respect to the housing means in response to insertion of the piercing means through the opening.

19. The system of claim 15, further comprising locking means for automatically limiting movement between the barrier means and the housing means upon withdrawing the piercing means through the opening.

20. The system of claim 15, wherein the piercing means further comprises a securing feature to prevent withdrawing the end of the piercing means through a proximal end of the housing means.

* * * * *